US010083335B2

United States Patent
Zhang

(10) Patent No.: US 10,083,335 B2
(45) Date of Patent: Sep. 25, 2018

(54) IMAGE ACQUISITION APPARATUS, TERMINAL DEVICE, LIQUID CRYSTAL TERMINAL DEVICE AND IMAGE ACQUISITION METHOD

(71) Applicant: Vkansee Technology Company Ltd., Shenzhen, Guangdong (CN)

(72) Inventor: Mingfang Zhang, Guangdong (CN)

(73) Assignee: Vkansee Technology Company Ltd., Shenzhen, Guangdong (CN)

( * ) Notice: Subject to any disclaimer, the term of this patent is extended or adjusted under 35 U.S.C. 154(b) by 6 days.

(21) Appl. No.: 15/320,243

(22) PCT Filed: Dec. 26, 2014

(86) PCT No.: PCT/CN2014/095140
§ 371 (c)(1),
(2) Date: Dec. 19, 2016

(87) PCT Pub. No.: WO2015/192630
PCT Pub. Date: Dec. 23, 2015

(65) Prior Publication Data
US 2017/0193270 A1     Jul. 6, 2017

(30) Foreign Application Priority Data

Jun. 20, 2014    (CN) .......................... 2014 1 0281380

(51) Int. Cl.
*G06K 9/00*       (2006.01)
*F21V 8/00*       (2006.01)
(Continued)

(52) U.S. Cl.
CPC ........ *G06K 9/00013* (2013.01); *A61B 5/1172* (2013.01); *G02B 6/005* (2013.01);
(Continued)

(58) Field of Classification Search
CPC ............. G06K 9/0004; G06K 9/00046; G06K 9/00087; G06K 9/00892; H04N 5/2256; H04N 5/23229
(Continued)

(56) References Cited

U.S. PATENT DOCUMENTS 6,154,285 A * 11/2000 Teng .................... A61B 5/1172
356/445
6,185,319 B1    2/2001   Fujiwara
(Continued)

FOREIGN PATENT DOCUMENTS

CN         1381810 A     11/2002
CN         1392507 A      1/2003
(Continued)

OTHER PUBLICATIONS

Shogenji et al., Application of Compound-eye Imaging Module for Security Systems, May 2005, 17E Technical Report vol. 29, pp. 13-16, English abstract only.

*Primary Examiner* — Solomon G Bezuayehu
(74) *Attorney, Agent, or Firm* — Rudy J. Ng; Bret E. Field; Bozicevic, Field & Francis LLP

(57) ABSTRACT

An image acquisition apparatus, a terminal device, a liquid crystal terminal device, and an image acquisition method are provided. The image acquisition apparatus (8) includes a light guide plate (1) and an image scanner (16) disposed to be spaced apart from the light guide plate (1), a light source (2) being disposed at a side of the light guide plate (1). The image acquisition apparatus (8) is integrated into the terminal device (7). The liquid crystal terminal device includes a LCD panel (11), a backlight element (12) and the image acquisition apparatus (8), an image scanner (16) of the image acquisition apparatus (8) being disposed in the backlight element (12). The image acquisition method includes: making at least part of light emitted by the light source (2)
(Continued)

enter and propagate inside the light guide plate (1) through TIR, and acquiring an image of an object on the other side of the light guide plate (1) by an image scanner (16). An ultra-thin image acquisition apparatus (8), terminal device (7) and liquid crystal terminal device formed based on a waveguide principle and a multi-pinhole imaging principle significantly reduce the size and thickness of an image acquisition module in the device and greatly facilitate the implementation of mobile devices and embedded devices in which an image acquisition function is required.

5 Claims, 11 Drawing Sheets

(51) Int. Cl.
  *G02F 1/1333* (2006.01)
  *G06K 9/20* (2006.01)
  *A61B 5/1172* (2016.01)
  *G02F 1/1335* (2006.01)

(52) U.S. Cl.
  CPC ......... *G02F 1/13338* (2013.01); *G06K 9/209* (2013.01); *G06K 9/2036* (2013.01); *G02F 1/133615* (2013.01)

(58) Field of Classification Search
  USPC .................................. 382/124, 115, 126, 119
  See application file for complete search history.

(56) References Cited

U.S. PATENT DOCUMENTS

| | | | |
|---|---|---|---|
| 2008/0122803 A1 | 5/2008 | Izadi et al. | |
| 2010/0208954 A1* | 8/2010 | Wu | G06K 9/00046 382/126 |
| 2016/0034772 A1* | 2/2016 | Betensky | G06K 9/0004 382/124 |

FOREIGN PATENT DOCUMENTS

| | | |
|---|---|---|
| CN | 1474212 A | 2/2004 |
| CN | 101034332 A | 9/2007 |
| CN | 101361095 A | 2/2009 |
| CN | 102096815 A | 6/2011 |
| CN | 102419815 A | 4/2012 |
| CN | 103942537 A | 7/2014 |
| CN | 104182727 A | 12/2014 |
| CN | 204028936 U | 12/2014 |
| JP | 2010094499 A | 4/2010 |
| JP | 2010282523 A | 12/2010 |
| JP | 2012-73101 A | 4/2012 |
| KR | 20020081070 A | 10/2002 |
| TW | 200701092 A | 1/2007 |
| WO | WO2009090217 A1 | 7/2009 |

* cited by examiner

IMAGE ACQUISITION APPARATUS, TERMINAL DEVICE, LIQUID CRYSTAL TERMINAL DEVICE AND IMAGE ACQUISITION METHOD

This application claims priority to Chinese Patent Application NO. 201410281380.0, titled "Ultra-thin fingerprint, palmprint acquisition apparatus, and fingerprint, palmprint acquisition method", filed on Jun. 20, 2014, the entire contents of which are incorporated herein by reference.

TECHNICAL FIELD

The present disclosure relates to the field of image acquisition, and in particular, to an ultra-thin image acquisition apparatus, a terminal device, a liquid crystal terminal device, and an image acquisition method.

BACKGROUND

There are mainly two types of the existing fingerprint acquisition apparatuses. One is to acquire a fingerprint by sensing a fingerprint texture directly by means of a semiconductor chip. The other is an optical fingerprint acquisition apparatus, which acquires a fingerprint image as it is formed due to differences of light intensity between a ridge and a valley when the finger touches the device surface. However, the fingerprint acquisition method based on the semiconductor chip has disadvantages of insufficient anti-static and anti-corrosion ability, and poor fingerprint acquisition sensitivity. As shown in FIG. 1, in the existing optical fingerprint and palmprint acquisition apparatus, an optical element for carrying a fingerprint and palmprint mainly include a prism 1', a light source 2' disposed on one side of the prism, and an image sensor 3' and lens 4' disposed on the other side of the prism. The vertical dimension of the prism 1' is large, and even if other optical elements are used to carry the fingerprint, the vertical dimension of the optical lens alone is too large. Meanwhile, too many optical elements are used in most of the existing acquisition apparatuses, resulting in an overall too large vertical dimension of the acquisition apparatus.

As mentioned above, the optical fingerprint acquisition apparatus in FIG. 1 has numerous disadvantages, even if only applied to acquire a single fingerprint. However, if the optical fingerprint and palmprint acquisition apparatus is applied to acquire a palmprint, since the palmprint is significantly larger than the single fingerprint, a larger prism, and more lenses and light sensing elements are required. Because the shape and structure of the prism, the larger the surface of the prism for carrying the fingerprint or palmprint, the larger the volume of the prism. Thus, the physical dimensions of the overall fingerprint and palmprint acquisition apparatus is even larger, increasing the cost.

With the development of science and technology and the continuous increase in public security awareness, beyond the traditional security field, the fingerprint and palmprint acquisition apparatus is more and more widely used in portable electronic products, such as mobile phones, notebooks, or tablets.

With the development trend of ultra-thin electronic products, the large size of the existing optical fingerprint and palmprint acquisition apparatus makes it difficult to meet the current requirements in electronic products. On the other hand, a fingerprint and palmprint acquisition apparatus directly by a semiconductor chip cannot better meet the ultra-thin requirements in existing electronic products due to lower aesthetic design and high cost.

Therefore, how to reduce the thickness of the optical fingerprint acquisition apparatus becomes a technical problem to be solved.

SUMMARY

In view of above problems, an image acquisition apparatus, a terminal device, a liquid crystal terminal device, and an image acquisition method are provided according to the disclosure. The image acquisition apparatus has a compact and ultra-thin structure, significantly reducing the size and thickness of an image acquisition module in the terminal device and the liquid crystal terminal device, and reducing the cost.

In order to achieve the above objective, an image acquisition apparatus is provided according to the disclosure, which includes:

a light guide plate;

a light source for emitting light into the light guide plate, wherein the light source is disposed at a side of the light guide plate; and an image scanner for acquiring an image of objects on the light guide plate, wherein the image scanner is disposed to be spaced apart from the light guide plate.

Further, the image scanner includes a pinhole imaging plate disposed to be spaced apart from the light guide plate, wherein the pinhole imaging plate is provided with at least one imaging pinhole, and at least one image sensor is disposed to be spaced apart from the other side of the pinhole imaging plate and corresponds to the imaging pinhole.

Further, vertical distance from a surface of the light guide plate away from the pinhole imaging plate to a center plane of the imaging pinhole is defined as object distance $h_{object}$, and the object distance $h_{object}$ satisfies a formula of $$h_{object} \geq \frac{\sqrt{2}\,r}{2tg(\alpha/2)},$$

wherein r represents a distance between centers of two adjacent imaging pinholes, and α represents angular field of view of the imaging pinhole.

Further, the distance r between the centers of two adjacent imaging pinholes satisfies a formula of $r \geq 2 \cdot h_{image} tg(\alpha/2)$, wherein $h_{image}$ represents an image distance, which is vertical distance from the image sensor to the center plane of the imaging pinhole, and α represents the angular field of view of the imaging pinhole.

Further, the aperture of the imaging pinhole is in a range from 0.001 mm to 1 mm, the thickness of the pinhole imaging plate is in a range from 0.005 mm to 5 mm, and the thickness of the light guide plate is in a range from 0.1 mm to 5 mm.

Further, an optical filter is disposed between the imaging pinhole and the image sensor.

Further, a correction lens is disposed on either or both sides of the imaging pinhole.

Further, the image acquisition apparatus includes at least one lens disposed to be spaced apart from the light guide plate, and at least one image sensor is disposed to be spaced apart from the other side of the lens.

A terminal device is provided, which includes the image acquisition apparatus.

A terminal device is provided, which includes a light guide plate and a display panel disposed to be spaced apart from the light guide plate, wherein a light source for emitting at least part of light into the light guide plate is disposed at a side of the light guide plate, the display panel is taken as a pinhole imaging plate, the display panel is provided with at least one imaging pinhole, and at least one image sensor is disposed to be spaced apart from the other side of the display panel and corresponds to the imaging pinhole.

Further, vertical distance from a surface of the light guide plate away from the display panel to a center plane of the imaging pinhole is defined as object distance $h_{object}$, and the object distance $h_{object}$ satisfies a formula of $$h_{object} \geq \frac{\sqrt{2}\,r}{2tg(\alpha/2)},$$

wherein r represents a distance between centers of two adjacent imaging pinholes, and α represents angular field of view of the imaging pinhole.

Further, the distance r between the centers of two adjacent imaging pinholes satisfies a formula of $r \geq 2 \cdot h_{image} tg(\alpha/2)$, wherein $h_{image}$ represents an image distance, which is vertical distance from the image sensor to the center plane of the imaging pinhole, and α represents the angular field of view of the imaging pinhole.

A terminal device is provided, which includes a light guide plate and a display panel disposed to be spaced apart from the light guide plate, wherein a light source for emitting at least part of light into the light guide plate is disposed at one side of the light guide plate, the display panel is provided with at least one transparent hole, at least one lens is disposed to be spaced apart from the other side of the display panel and corresponds to the transparent hole, and at least one image sensor is disposed to be spaced apart from the other side of the lens.

A liquid crystal terminal device is provided, which includes a liquid crystal display (LCD) screen, wherein the LCD screen comprises a LCD panel, a backlight element and the image acquisition apparatus, wherein the LCD panel is disposed between a light guide plate and an image scanner of the image acquisition apparatus;

the backlight element comprises a reflective sheet, a back plate and at least one layer of optical film disposed between the reflective sheet and the LCD panel, wherein the image scanner is disposed between the reflective sheet and the back plate, a via is disposed at a position corresponding to the image scanner on the reflective sheet, and a light transmitting window is disposed on the optical film at a position corresponding to the via.

A liquid crystal terminal device is provided, which includes a LCD screen including a LCD panel, a backlight element and the image acquisition apparatus, wherein, the LCD panel is disposed between a light guide plate and an image scanner of the image acquisition apparatus, and the backlight element is disposed between the LCD panel and the image scanner;

the backlight element includes a reflective sheet, a back plate and at least one layer of optical film disposed between the reflective sheet and the LCD panel, wherein a first via and a second via are respectively disposed at a position corresponding to the image scanner on the reflective sheet and the back plate, and a light transmitting window is disposed on the optical film at a position corresponding to the respective first via and second via.

A liquid crystal terminal device is provided, which includes a LCD screen, wherein the LCD screen comprises a LCD panel, a backlight element disposed at a side of the LCD panel and a light guide plate disposed to be spaced apart from the other side of the LCD panel, wherein a light source is disposed on one side of the light guide plate, and the backlight element comprises a reflective sheet, a back plate and at least one layer of optical film disposed between the reflective sheet and the LCD panel, wherein an image sensor is disposed between the reflective sheet and the back plate, spaced apart from the reflective sheet, wherein, the reflective sheet acts as a pinhole imaging plate, at least one imaging pinhole is disposed on the reflective sheet at a position corresponding to the image sensor, the imaging pinhole is disposed to be spaced apart from the image sensor, and a light transmitting window is disposed on the optical film at a position corresponding to the imaging pinhole.

A liquid crystal terminal device is provided, which includes a LCD screen, wherein the LCD screen comprises a LCD panel, a backlight element disposed at a side of the LCD panel and a light guide plate disposed to be spaced apart from the other side of the LCD panel, wherein a light source is disposed at a side of the light guide plate, and the backlight element comprises a reflective sheet, a back plate and at least one layer of optical film disposed between the reflective sheet and the LCD panel, wherein at least one image sensor is disposed to be spaced apart from the other side of the back plate, wherein the reflective sheet and the back plate together act as a pinhole imaging plate, at least one imaging pinhole is disposed on the reflective sheet together with the back plate at a position corresponding to the image sensor, the image sensor is disposed to be spaced apart from the imaging pinhole, and a light transmitting window is disposed on the optical film at a position corresponding to the imaging pinhole.

A liquid crystal terminal device is provided, which includes a LCD screen, wherein the LCD screen comprises a LCD panel and a backlight element disposed at a side of the LCD panel, wherein the LCD panel is taken as a light guide plate, wherein a light source is disposed on a side of the LCD panel, and the backlight element comprises a reflective sheet, a back plate and at least one layer of optical film disposed between the reflective sheet and the LCD panel, wherein at least one image sensor is disposed between the reflective sheet and the back plate, spaced apart from the reflective sheet, wherein, the reflective sheet acts as a pinhole imaging plate, at least one imaging pinhole is disposed on the imaging plate at a position corresponding to the image sensor, the image sensor is disposed to be spaced apart from the imaging pinhole, and a light transmitting window is disposed on the optical film at a position corresponding to the imaging pinhole.

A liquid crystal terminal device is provided, which includes a LCD screen, wherein the LCD screen comprises a LCD panel and a backlight element disposed at a side of the LCD panel, wherein the LCD panel is taken as a light guide plate, wherein a light source is disposed at a side of the LCD panel, and the backlight element comprises a reflective sheet, a back plate and at least one layer of optical film disposed between the reflective sheet and the LCD panel, wherein at least one image sensor is disposed to be spaced apart from the other side of the back plate, wherein the reflective sheet and the back plate together act as a pinhole imaging plate, at least one imaging pinhole is disposed on the reflective sheet together with the back plate at a position corresponding to the image sensor, the image sensor is disposed to be spaced apart from the imaging pinhole, and a light transmitting window is disposed on the optical film at a position corresponding to the imaging pinhole.

Further, vertical distance from a surface of the light guide plate away from the pinhole imaging plate to the center plane of the imaging pinhole is defined as object distance $h_{object}$, and the object distance $h_{object}$ satisfies a formula of $$h_{object} \geq \frac{\sqrt{2}\,r}{2tg(\alpha/2)},$$

wherein r represents a distance between centers of two adjacent imaging pinholes, and α represents angular field of view of the imaging pinhole.

Further, the distance r between the centers of two adjacent imaging pinholes satisfies a formula of $r \geq 2 \cdot h_{image} tg(\alpha/2)$, wherein $h_{image}$ represents an image distance, which is vertical distance from the image sensor to the center plane of the imaging pinhole, and α represents the angular field of view of the imaging pinhole.

An image acquisition method for the image acquisition apparatus is provided, which includes:

making at least part of light emitted by the light source enter and propagate inside a light guide plate through total internal reflection; and acquiring an image of an object above the light guide plate by an image scanner.

Further, the acquiring an image of an object above the light guide plate by an image scanner includes:

establishing multiple scanning regions corresponding to multiple imaging pinholes for the object above the light guide plate, wherein adjacent scanning regions are overlapping with each other;

capturing, by the image sensor, multiple imaging regions corresponding to multiple imaging pinholes as partial images of the object above the light guide plate being scanned in corresponding scanning regions, wherein the partial images, wherein the partial images do not overlap with each other; and stitching together the partial images in each of the imaging regions to obtain a complete image of the object being scanned.

An image acquisition method for the liquid crystal terminal device is provided, which includes:

putting a LCD panel into a transparent state in response to a control signal;

making at least part of light emitted by the light source enter and propagate inside a light guide plate through total internal reflection; and acquiring an image of an object above the light guide plate by the image scanner.

Further, the acquiring an image of an object above the light guide plate by the image scanner specifically includes:

establishing multiple scanning regions corresponding to multiple imaging pinholes for the object above the light guide plate, wherein adjacent scanning regions are overlapping with each other;

capturing multiple imaging regions corresponding to multiple imaging pinholes one by one by the image sensor as partial images of the object above the light guide plate being scanned in corresponding scanning regions, wherein the partial images do not overlap with each other; and stitching together the partial images in each of the imaging regions to obtain a complete image of the object being scanned.

Further, the acquiring an image of an object above the light guide plate by the image scanner specifically includes:

establishing multiple scanning regions corresponding to multiple imaging pinholes for the object above the light guide plate, wherein adjacent scanning regions are overlapping with each other;

putting areas of the LCD panel into a transparent state, one by one corresponding to respective scanning regions, in response to a control signal;

capturing multiple imaging regions corresponding to multiple imaging pinholes one by one by the image sensor as partial images of the object above the light guide plate being scanned in corresponding scanning regions, wherein the partial images do not overlap with each other; and stitching together the partial images in each of the imaging regions to obtain a complete image of the object being scanned.

With the above-described solutions, the image acquisition apparatus, the terminal device, the liquid crystal terminal device and the image acquisition method according to the disclosure have the following advantages.

1. Using frustrated total internal reflection of the light in an ultra-thin light guide plate instead of an optical prism, and deposing the light source on a side of the light guide plate, and using a compact structure of pinhole imaging plate and image sensor, the thickness of the imaging acquisition apparatus, terminal device, and liquid crystal terminal device is greatly reduced compared with the traditional optical acquisition device.

2. The image acquisition apparatus according to the disclosure is integrated into a terminal device or a liquid crystal liquid terminal device, adding fingerprint and/or palmprint acquisition function with fewer additional components and lower cost.

DESCRIPTION OF THE EMBODIMENTS

In the following, the disclosure is described in detail in conjunction with the drawings.

Figure 1:
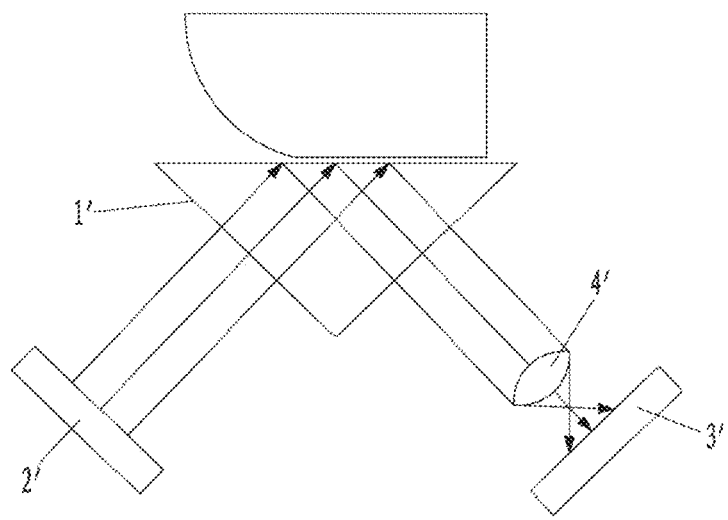
FIG. 1 is a schematic diagram of a fingerprint, palmprint acquisition apparatus in the prior art.
Figure 2:
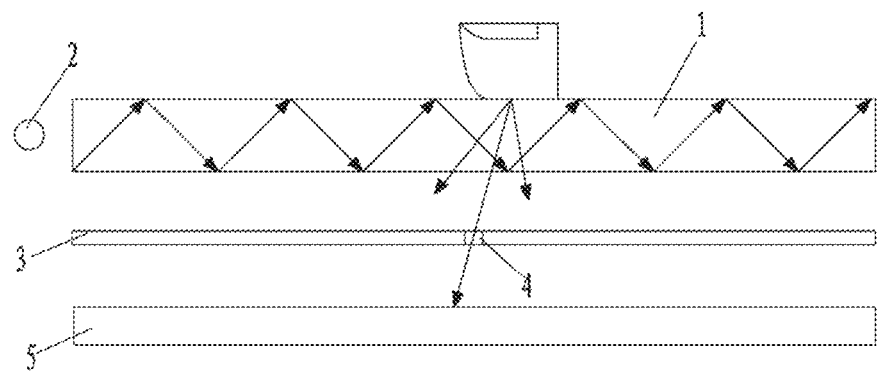
FIG. 2 is a schematic diagram of an image acquisition apparatus according to a first embodiment of the present disclosure.

FIG. 2 shows a schematic diagram of an image acquisition apparatus according to a first embodiment of the present disclosure. The image acquisition apparatus includes a light guide plate 1 and an image scanner disposed to be spaced apart from the light guide plate 1. The light guide plate 1 may be made of a variety of materials, such as glass or other transparent materials. In this embodiment, the image scanner is disposed below the light guide plate 1, and a light source 2 is disposed at a side of the light guide plate 1. The light source 2 may be fixed at the left side of the light guide plate 1 through a support element. In this embodiment, the image scanner includes a pinhole imaging plate 3 disposed to be spaced apart from the light guide plate 1, and the pinhole imaging plate 3 is disposed below the light guide plate 1. In this embodiment, one or more imaging pinholes 4 may be disposed on the pinhole imaging plate 3. A image sensor 5 is disposed to be spaced apart from the other side (that is, the lower surface) of the pinhole imaging plate 3 at a position corresponding to the imaging pinhole 4. The image sensor 5 may include a photoelectric converting element and an image signal processing element. The light emitted from the light source 2 enters the light guide plate 1 from the left side of the light guide plate 1, and at least part of the light in the light guide plate 1 propagates by total internal reflection (TIR). Specifically, whether all or only part of the light in the light guide plate 1 propagates by TIR poses no limitation to this and the following embodiments, an image of the object can be successfully acquired as long as there is sufficient light propagating by TIR.

The light guide plate 1 is used as the surface to be touched by a finger (the object) to be scanned. When no finger is touching the light guide plate 1, the light emitted from the light source 2 enters the light guide plate 1, and at least part of the light in the light guide plate 1 propagates by TIR. When a finger is touching the surface of the light guide plate 1, because of the refractive index of the object surface is different from that of air (there is secretion on the surface of the finger which has a refractive index similar to that of the water), thus the TIR condition of the light in the light guide plate 1 is frustrated. Part of the light is projected onto the finger surface leaking from the light guide plate 1; part of the light reflected on the surface of the finger is diffusing in various angles; part of that light will pass the imaging pinhole 4 to form a fingerprint image on the image sensor 5 below the pinhole pinhole imaging plate 3.

A fingerprint acquisition method for the image acquisition apparatus according to the embodiment includes the following steps.

At least part of light emitted by the light source 2 enters the light guide plate 1, wherein at least part of the light propagates by TIR in the light guide plate 1.

An image of a finger on a surface of the light guide plate 1 is acquired by the image sensor 5 in the image scanner.

Figure 3:
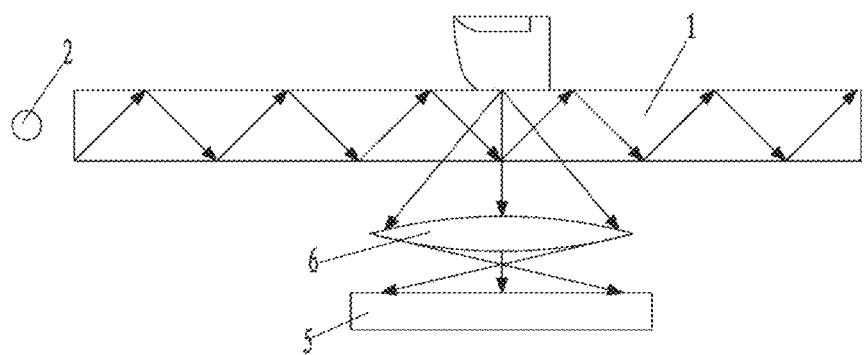
FIG. 3 is a schematic diagram of an image acquisition apparatus according to a second embodiment of the present disclosure.

FIG. 3 shows a schematic diagram of an image acquisition apparatus according to a second embodiment of the present disclosure, of which the structure is mostly the same as that in the embodiment shown in FIG. 2. The difference is that the image acquisition apparatus includes a lens 6 disposed to be spaced apart from the light guide plate 1. In this embodiment, the lens 6 is disposed below the light guide plate 1, and the image sensor 5 is disposed to be spaced apart from the other surface (that is, lower surface) of the lens 6. In use, the light emitted from the light source 2 enters the light guide plate 1, and at least part of the light propagates by TIR in the light guide plate 1. When a finger is touching the surface of the light guide plate 1, the TIR of the light in the light guide plate 1 is frustrated. Part of the light is projected onto the finger surface leaking from the light guide plate 1; part of the light reflected on the surface of the finger is diffusing in various angles; part of that light is refracted on the lens 6 to form a fingerprint image, which is acquired by the image sensor 5 below the lens 6.

The embodiments described above with reference to FIG. 2 and FIG. 3 may also be applied to acquire the image of the palm (palmprint), or the fingerprint and palmprint at the same time.

Figure 4A:
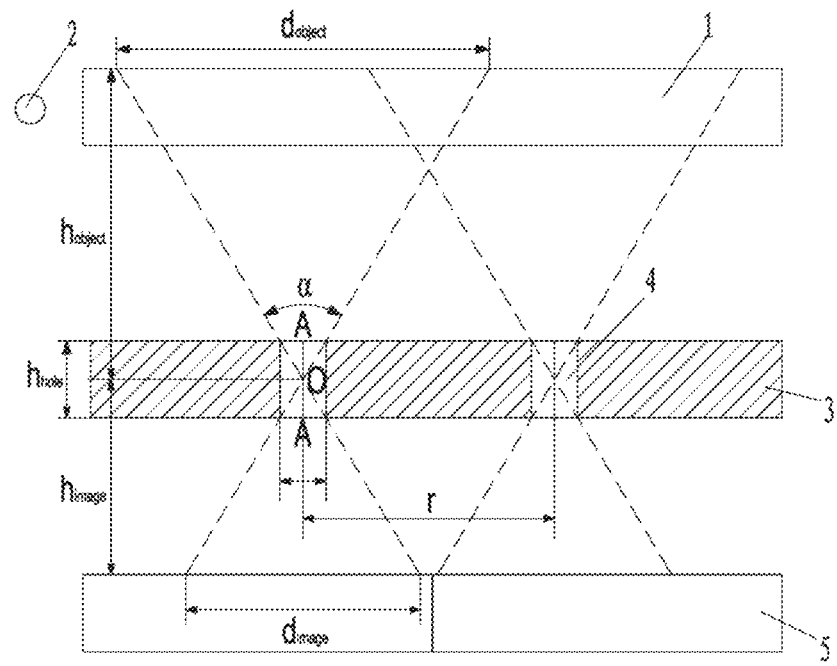
FIG. 4A is a schematic diagram of an image acquisition apparatus according to a third embodiment of the present disclosure.

FIG. 4A shows a schematic diagram of an image acquisition apparatus according to a third embodiment of the present disclosure, of which the structure is mostly the same as that in the embodiment shown in FIG. 2. The difference is that multiple imaging pinholes 4 are disposed on the pinhole imaging plate 3 of the image acquisition apparatus, and the image sensors 5 are disposed below the pinhole imaging plate 3 at positions corresponding to the imaging pinholes 4. The reason why the multiple imaging pinholes 4 are disposed on the pinhole imaging plate 3 is that when the distances between light guide plate 1, pinhole imaging plate 3, and image sensor 5 are small, that is, the overall thickness is small, the field of view of a single imaging pinhole 4 is small, and thus only part of the fingerprint can be scanned. Therefore, multiple imaging pinholes 4 are needed to increase the imaging area of the fingerprint. In this embodiment, the number of the imaging pinholes 4 and the number of the image sensors 5 both are set to be four.

A distance from a surface (that is, the upper surface) of the light guide plate 1 away from the pinhole imaging plate 3 to the center O of an axis A-A of the imaging pinhole 4 is object distance $h_{object}$. In this embodiment, the object distance $h_{object}$ satisfies the formula:

$$h_{object} \geq \frac{\sqrt{2}\,r}{2tg(\alpha/2)},$$

where r represents a distance between the centers of two adjacent imaging pinholes 4, and α represents the angular field of view of the imaging pinhole 4. This ensures that the detected fingerprint image is complete and no areas are omitted. The scanning region is defined as a visual range on the top surface of the light guide plate 1 corresponding to the angular field of view of each of the imaging pinholes 4. Meanwhile, the distance r between the centers of two adjacent imaging pinholes 4 satisfies the formula: $r \geq 2 \cdot h_{image} tg(\alpha/2)$, wherein $h_{image}$ represents the image distance, which is the distance from the image sensor 5 to the center plane of the imaging pinhole 4, and α represents the angular field of view of the imaging pinhole. In this way, it is further ensured that images of the imaging regions corresponding to the respective imaging pinholes 4 are not overlapping with each other, assuring the quality of the image acquisition. The imaging region is defined as a sensing range on the image sensor 5 corresponding to the angular field of view a of each of the imaging pinholes 4.

In this embodiment, assuming that $h_{image}$ is equal to 3 millimeters, and α is equal to 120°, then r≥6√3 millimeters, that is, r is greater than or equal to 10.392 millimeters. The object distance $h_{object}$ is greater than or equal to 4.242 millimeters, so that the imaging regions of the imaging pinholes 4 are not overlapping.

The above-mentioned formulas $$h_{object} \geq \frac{\sqrt{2}\,r}{2tg(\alpha/2)} \text{ and } r \geq 2 \cdot h_{image} tg(\alpha/2)$$

are derived as follows.

(1) Assuming that the thickness of the pinhole imaging plate 3 is $h_{hole}$, and the aperture of the imaging pinhole 4 is $d_{hole}$;

(2) Referring to FIG. 4A, the imaging angle α may be calculated based on the above-mentioned $h_{hole}$ and $d_{hole}$, that is, $tg(\alpha/2)=(d_{hole}/2)/(h_{hole}/2)$, then $$\alpha = 2\,arctg(d_{hole}/h_{hole}) \quad \text{(formula 1)}$$

(3) The image distance $h_{image}$ is given, and then the diameter $d_{image}$ of the imaging region may be calculated as, referring to FIG. 4A, $$d_{image} = 2 \cdot h_{image} \cdot tg(\alpha/2) \quad \text{(formula 2)}$$

(4) As the imaging regions must not overlap, the distance r between the centers of two adjacent imaging pinholes may be calculated as, $r \geq d_{image}$, that is, $$r \geq 2 \cdot h_{image} \cdot tg(\alpha/2) \quad \text{(formula 3)}$$

Figure 4B:
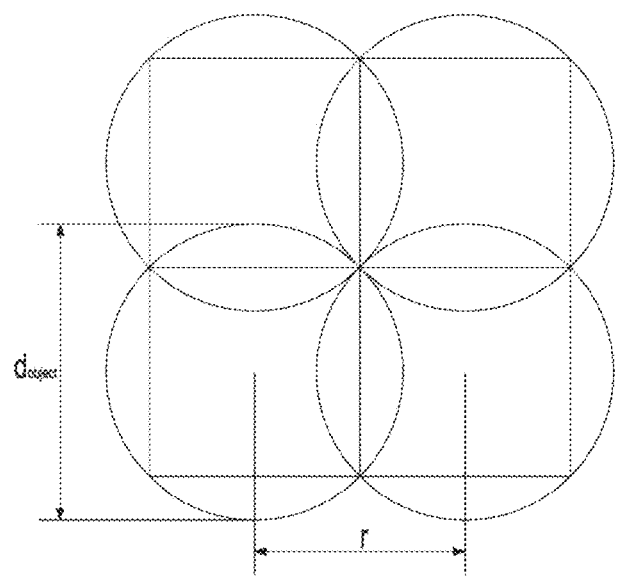
FIG. 4B is a schematic top view of an image scanning region as shown in FIG. 4A.

(5) In conjunction with FIG. 4A and FIG. 4B, to ensure that the fingerprint image is complete and no area is omitted, adjacent image scanning regions must overlap, that is, $d_{object} \geq \sqrt{2}\,r$;

and since $d_{object} = 2h_{object} \cdot tg(\alpha/2)$, $2h_{object} \cdot tg(\alpha/2) \geq \sqrt{2}\,r$;

which can be simplified to $$h_{object} \geq \frac{\sqrt{2}\,r}{2tg(\alpha/2)} \quad \text{(formula 4)}$$

An image acquisition method for the image acquisition apparatus according to the embodiment includes the following steps.

At least part of light emitted by the light source 2 enters the light guide plate 1, and then propagates by TIR;

As the number of the imaging pinholes 4 is four, four scanning regions are established on the upper surface of the light guide plate 1, so that adjacent scanning regions do overlap;

Images of partial fingerprints in the respective scanning regions are obtained by using the image sensor 5 in the image scanner through the imaging pinholes 4 in the pinhole imaging plate 3, so that partial fingerprint images in respective adjacent imaging regions do not overlap; and The images of the partial fingerprints are stitched together to form a complete fingerprint image, and after further image enhancement processing a final fingerprint image is obtained.

The light guide plate 1 is used to provide a touch surface for the finger or palm, facilitating the acquisition of fingerprint and palmprint images. In addition, this protects the components under the light guide plate 1.

This embodiment has all the advantages of the image acquisition apparatus according to the embodiment shown in FIG. 2. But compared with the embodiment shown in FIG. 2, the distances among the light guide plate 1, the pinhole imaging plate 3 and the image sensor 5 are further reduced, without affecting the image acquisition, and the stitching and cutting processes are added in the compositing process of the fingerprint.

In the embodiments described above, the aperture of the imaging pinhole 4 is in a range from 0.001 mm to 1 mm. For the best imaging effects, shorter imaging distance, faster processing and other considerations, the aperture of the imaging pinhole 4 may be chosen within the range from 0.01 mm to 0.1 mm, but preferably 0.05 mm. The thickness of the pinhole imaging plate 3 is in a range from 0.005 mm to 5 mm, and preferably, in the range from 0.001 mm to 5 mm, and the thickness of the light guide plate 1 is in a range from 0.1 mm to 5 mm. An optical filter may be disposed between the imaging pinhole 4 and the image sensor 5 to control the uniformity of the light. A correction lens may be disposed on either side or both sides of the imaging pinhole 4 to adjust the light, to obtain a clear image even if the imaging pinhole 4 has a large aperture.

Figure 5:
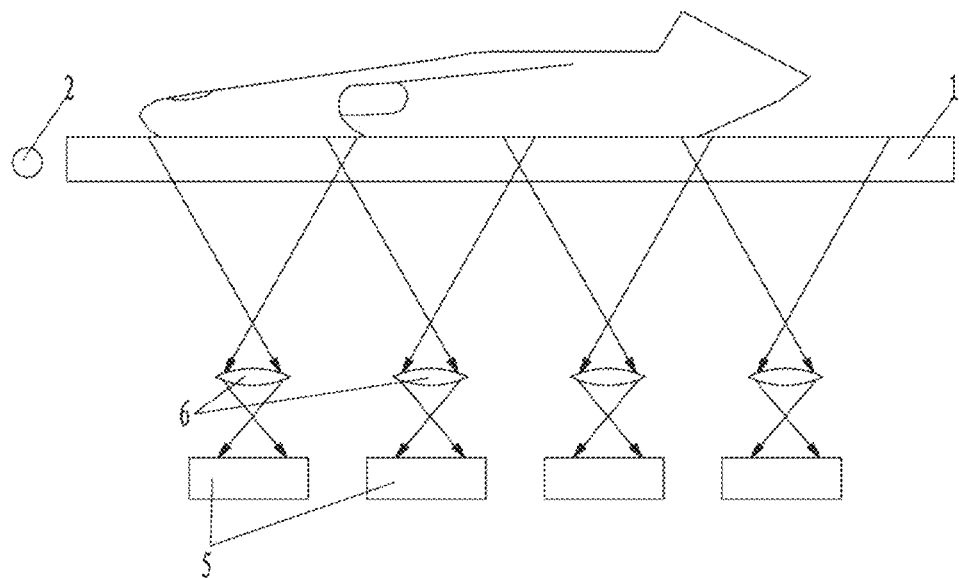
FIG. 5 is a schematic diagram of an image acquisition apparatus according to a fourth embodiment of the present disclosure.

FIG. 5 shows a schematic diagram of an image acquisition apparatus according to a fourth embodiment of the present disclosure. This embodiment is applied to acquire a palmprint image. The structure of the image acquisition apparatus is mostly the same as that in the embodiment shown in FIG. 3. The difference is that the image acquisition apparatus includes multiple lenses 6 disposed to be spaced apart from the light guide plate 1, and multiple image sensors 5 disposed to be spaced apart from the other sides (that is, the lower surfaces) of the lenses 6. In this embodiment, the number of the lenses 6 and the number of the image sensors 5 both are four.

An image acquisition method for the image acquisition apparatus according to the embodiment includes the following steps.

At least part of light emitted by the light source 2 enters the light guide plate 1, so that at least part of the light propagates by TIR;

As the number of the lenses 6 is four, four scanning regions are established on the surface of the light guide plate 1, so that the adjacent scanning regions overlap;

Images of partial palmprints in the respective scanning regions are obtained by using the image sensor 5 in the image scanner through multiple lenses 6, so that partial palmprint images in respective adjacent imaging regions do not overlap; and The images of partial palmprints are stitched together to form a complete palmprint image, and after further image enhancement processing, a final palmprint image is obtained.

In this embodiment, multiple lenses 6 and multiple photosensitive elements 5 are used to avoid the insufficient field of view of a single lens.

The structure of the embodiment may also be applied to acquire fingerprint images; several smaller lenses can be used in the acquisition of the fingerprint images; the images can be stitched together.

Figure 6:
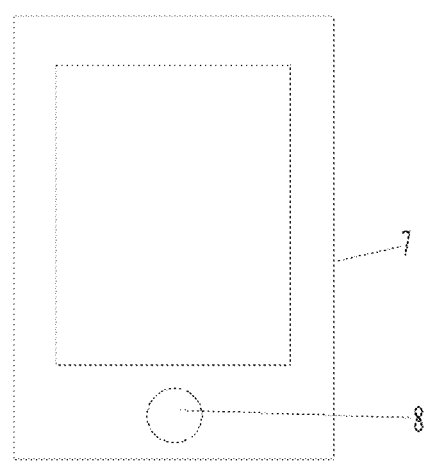
FIG. 6 is a schematic diagram of a terminal device according to a first embodiment of the present disclosure.

Each of the image acquisition apparatuses described above is applicable to various types of terminal devices. In practice, the image acquisition apparatus may be a stand-alone fingerprint scanner. FIG. 6 shows a schematic diagram of a terminal device according to a first embodiment of the present disclosure. A terminal device 7 is provided with the image acquisition apparatus 8 shown in any one of FIG. 1 to FIG. 5 described above. The image acquisition apparatus 8 is disposed at the edge of the terminal device 7. For example, the terminal device may be a mobile phone, and the image acquisition apparatus 8 may be disposed on the HOME key. When compared with a conventional fingerprint image acquisition apparatus, the image acquisition apparatus in the above embodiments has the advantage of a simple structure and ultra-thinness.

Figure 7:
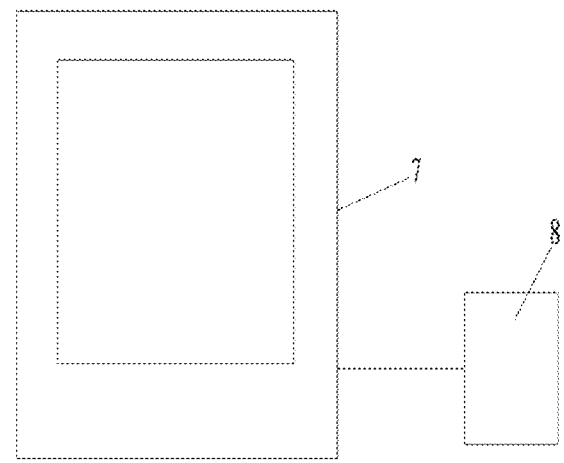
FIG. 7 is a schematic diagram of a terminal device according to a second embodiment of the present disclosure.

FIG. 7 shows a schematic diagram of a terminal device according to a second embodiment of the present disclosure, which includes the image acquisition apparatus 8 shown in any one of FIG. 1 to FIG. 5 described above, and the image acquisition apparatus 8 is a stand-alone device and is connected to the terminal device 7 through a cable and an interface.

Figure 8:
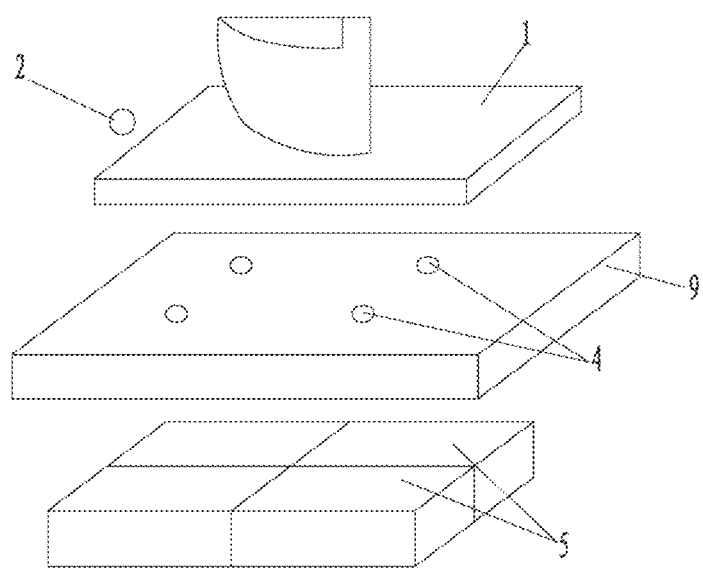
FIG. 8 is a schematic diagram of a terminal device according to a third embodiment of the present disclosure.

FIG. 8 shows a schematic diagram of a terminal device according to the third embodiment of the present disclosure. The terminal device includes a light guide plate 1 and a display panel 9 disposed to be spaced apart from the light guide plate 1. A light source 2 is disposed at the left side of the light guide plate 1, and the display panel 9 is a LCD panel. In this embodiment, the display panel 9 is disposed below the light guide plate 1 and is taken as a pinhole imaging plate, and at least one imaging pinhole 4 is disposed on the display panel 9. In this embodiment, four imaging pinholes 4 are disposed, and four image sensors 5 are disposed to be spaced apart from the other side (that is, the lower surface) of the display panel 9 at positions corresponding to the imaging pinholes 4. In this embodiment, each imaging pinhole 4 corresponds to one image sensor 5, and an image scanner is formed of the display panel 9 having multiple imaging pinholes 4 and multiple image sensors 5.

In this embodiment, a distance from a side (that is, the upper surface) of the light guide plate 1 away from the display panel 9 to the center plane of the imaging pinhole 4 is object distance $h_{object}$. In this embodiment, the object distance $h_{object}$ satisfies the formula of $$h_{object} \geq \frac{\sqrt{2}\,r}{2tg(\alpha/2)},$$

where r represents the distance between the centers of two adjacent imaging pinholes 4, and α represents the angular field of view of the imaging pinhole 4. Meanwhile, the distance r between the centers of two adjacent imaging pinholes 4 satisfies the formula of $r \geq 2 \cdot h_{image} tg(\alpha/2)$, wherein $h_{image}$ represents an image distance, which is a distance from the image sensor 5 to the center plane of the imaging pinhole 4, and α represents the angular field of view of the imaging pinhole.

In this embodiment, assuming that $h_{image}$ is equal to 2 millimeters, and α is equal to 120°, then $r \geq 4\sqrt{3}$, that is, r is greater than or equal to 6.928 millimeters. The object distance $h_{object}$ is greater than or equal to 2.828 millimeters, so that the imaging is performed through each imaging pinhole 4 separately, and the imaging pinholes 4 will not interfere with each other.

Reference may be made to the embodiment shown in FIG. 4A. In this embodiment, the display panel 9 is taken as a pinhole imaging plate, on which multiple imaging pinholes 4 are disposed. When no finger is touching the light guide plate 1, at least part of light entering the light guide plate 1 from the light source 2 propagates by TIR. When the finger is touching the light guide plate 1, the TIR of the light in the light guide plate 1 is frustrated. Part of the light is projected onto the finger surface leaking from the light guide plate 1; part of the light reflected on the surface of the finger is diffusing in various angles; part of that light passes the multiple imaging pinholes 4 to form multiple partial images of the fingerprint, and the multiple partial images of the fingerprint are stitched to form a complete fingerprint image, which is acquired by the image sensor 5 below the display panel 9.

In the embodiments described above, an optical filter may be disposed between the imaging pinhole 4 and the image sensor 5 to control the uniformity of the light. A correction lens may be disposed on either side or both sides of the imaging pinhole 4 to adjust the light, to obtain a clear image even if the imaging pinhole 4 has a large aperture.

Figure 9:
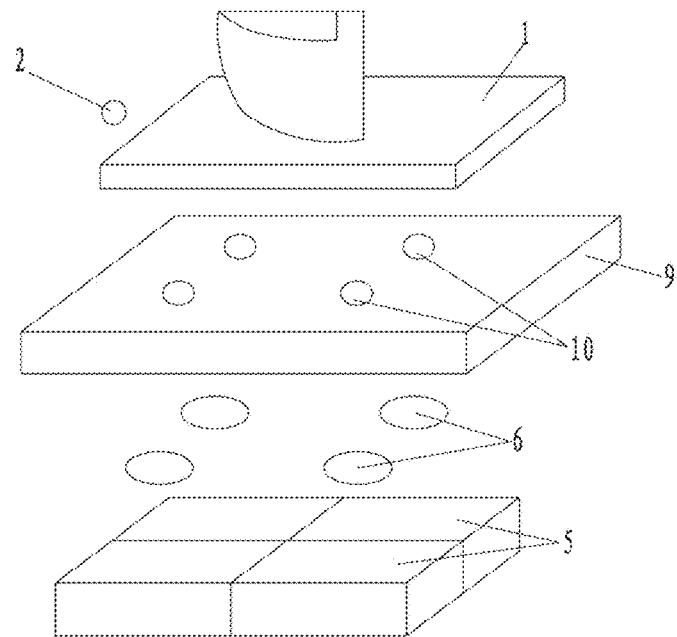
FIG. 9 is a schematic diagram of a terminal device according to a fourth embodiment of the present disclosure.

FIG. 9 shows a schematic diagram of a terminal device according to a fourth embodiment of the present disclosure. The terminal device includes a light guide plate 1 and a display panel 9 disposed below and spaced apart from the light guide plate 1. The display panel 9 is a LCD panel. A light source 2 for emitting at least part of light into the light guide plate 1 is disposed at the left side of the light guide plate 1, and at least part of the light entering the light guide plate 1 propagates by TIR. The display panel 9 is provided with at least one transparent hole 10. In this embodiment, four transparent holes 10 are disposed. At least one lens 6 is disposed to be spaced apart from the other side (the lower surface) of the display panel 9 and corresponds to the transparent hole 10. In this embodiment, one lens 6 is disposed correspondingly below each transparent hole 10, and a image sensor 5 is correspondingly disposed below each lens 6. An image scanner is formed of four lenses 6 and four image sensors 5.

In use, when a finger is touching the surface of the light guide plate 1, the TIR of the light in the light guide plate 1 is frustrated. Part of the light is projected onto the finger surface leaking from the light guide plate 1; part of the light reflected on the surface of the finger is diffusing in various angles; part of that light is projected onto the multiple lenses 6 through multiple transparent holes 10 and are refracted by the lenses 6 to form multiple partial images of the fingerprint. Finally, the multiple partial images of the fingerprint are stitched into one complete fingerprint image, which is acquired by the image sensors 5 below the lenses 6.

Although only the acquisition of the fingerprint is described in the two embodiments mentioned above, fingerprints of multiple fingers or multiple palmprints can be acquired at the same time. The acquisition of the palmprint has the same principle as the acquisition of the fingerprint, except that the upper surface of the light guide plate 1 has a different size.

Figure 10:
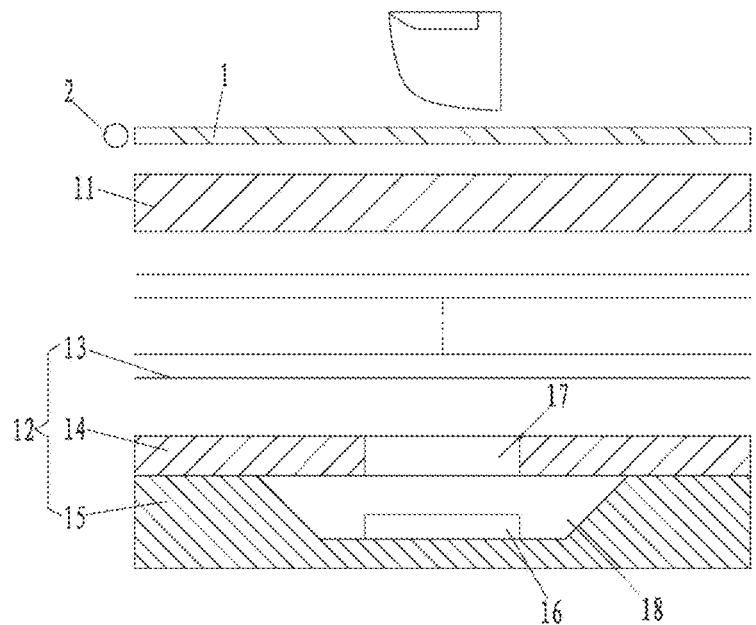
FIG. 10 is a schematic diagram of a liquid crystal terminal device according to a first embodiment of the present disclosure.

FIG. 10 shows a schematic diagram of a LCD terminal device according to a first embodiment of the present disclosure. The LCD terminal device includes a LCD screen. The LCD screen includes a LCD panel 11, a backlight element 12 disposed below the LCD panel 11, and the image acquisition apparatus according to any one of the embodiments shown in FIG. 1 to FIG. 5. In this embodiment, the LCD panel 11 is a transparent panel body composed of two (upper and lower) glass panels and liquid crystal molecules sandwiched between the two glass panels. From top to bottom, the backlight element includes one or more layers of optical film 13, a reflective sheet 14, and a back plate 15. The LCD panel 11 is disposed between a light guide plate 1 and an image scanner 16 of the image acquisition apparatus. The image scanner 16 may be an image scanner composed of at least one image sensor and a pinhole imaging plate having at least one imaging pinhole, or an image scanner composed of at least one image sensor and at least one lens. In this embodiment, the reflective sheet 14 is closely placed against the back plate 15. A via 17 is disposed at the center of the reflective sheet 14. A concave area 18 is disposed at a position corresponding to the via 17 on an upper surface of the back plate 15. The image scanner 16 is fixed within the concave area 18, and a light transmitting window is disposed on the optical film 13 at a position corresponding to the image scanner 16.

An image acquisition method for the LCD terminal device includes the following steps.

An LCD panel 11 is put into a transparent state in response to a control signal.

At least part of light emitted by the light source 2 at the left side of the light guide plate 1 enters and propagates inside the light guide plate 1 through TIR.

An image of a finger on an upper surface of the light guide plate 1 is acquired by using the image scanner 16 below the LCD panel 11 through the via 17 on the reflective sheet 14, the light transmitting window of the optical film 13, the LCD panel 11, and the light guide plate 1.

This embodiment can be used to acquire a fingerprint, a palmprint, or maybe an even an image of a face. In order to prevent image acquisition from being affected when the optical film 13 is not easy to transmit light or cannot transmit light, the light transmitting window is disposed on the optical film 13. If any optical film 13 is totally light transmitting, the optical film 13 is the light transmitting window. If any optical film 13 is not easy to transmit light or cannot transmit light, the light transmitting window on the optical film 13 may be a transparent hole or a light transmitting sheet.

In the embodiments described above, an aperture of the imaging pinhole 4 is in a range from 0.001 mm to 1 mm. For the best imaging effects, shorter imaging distance, processing and other considerations, the aperture of the imaging pinhole 4 may be chosen within the range from 0.01 mm to 0.1 mm, but preferably 0.05 mm. The thickness of the pinhole imaging plate 3 is in a range from 0.005 mm to 5 mm, and preferably, in the range from 0.001 mm to 5 mm, and the thickness of the light guide plate 1 is in a range from 0.1 mm to 5 mm. An optical filter may be disposed between the imaging pinhole 4 and the image sensor 5 to control the uniformity of the light. A correction lens may be disposed on either side or both sides of the imaging pinhole 4 to adjust the light, to obtain a clear image even if the imaging pinhole 4 has a large aperture.

Figure 11:
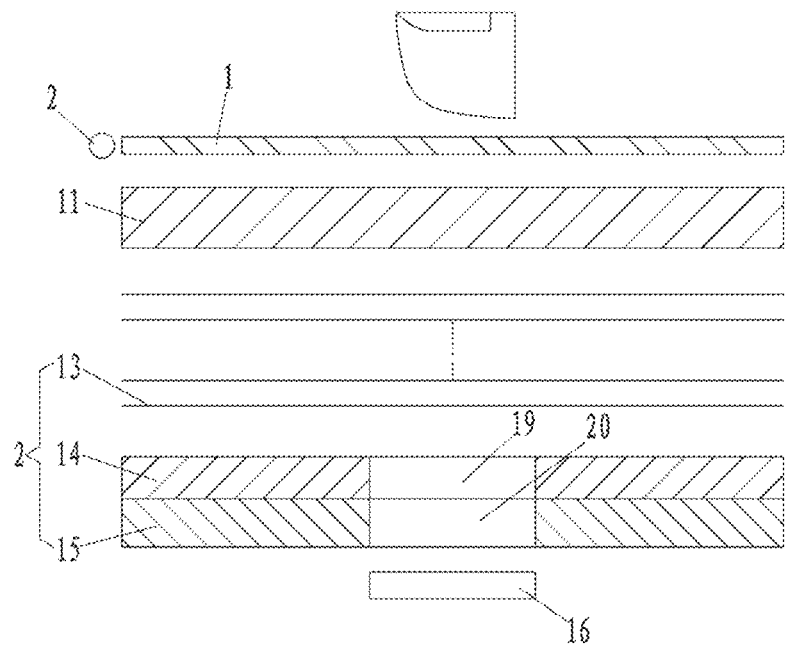
FIG. 11 is a schematic diagram of a liquid crystal terminal device according to a second embodiment of the present disclosure.

FIG. 11 shows a schematic diagram of a LCD terminal device according to the second embodiment of the present disclosure. Its structure is mostly the same as that in the embodiment shown in FIG. 10. The difference is that the image scanner 16 is disposed below the backlight element 12, a first via 19 and a second via 20 are respectively disposed on the reflective sheet 14 and the back plate 15 of the backlight element 12 at positions corresponding to the image scanner 16. The light transmitting windows are disposed on the optical film 13 at positions corresponding to the first via 19 and the second via 20.

In use, when the LCD panel 11 is in a transparent state, at least part of light from the light source 2 enters the light guide plate 1, and at least part of the light in the light guide plate 1 propagates by TIR. When a finger is touching an upper surface of the light guide plate 1, an image of a finger on an upper surface of the light guide plate 1 is acquired by using the image scanner 16 through the second via 20, the first via 19, the light transmitting window of the optical film 13, the LCD panel 11, and the light guide plate 1. Of course, this embodiment may also be used to detect a palmprint image.

Figure 12:
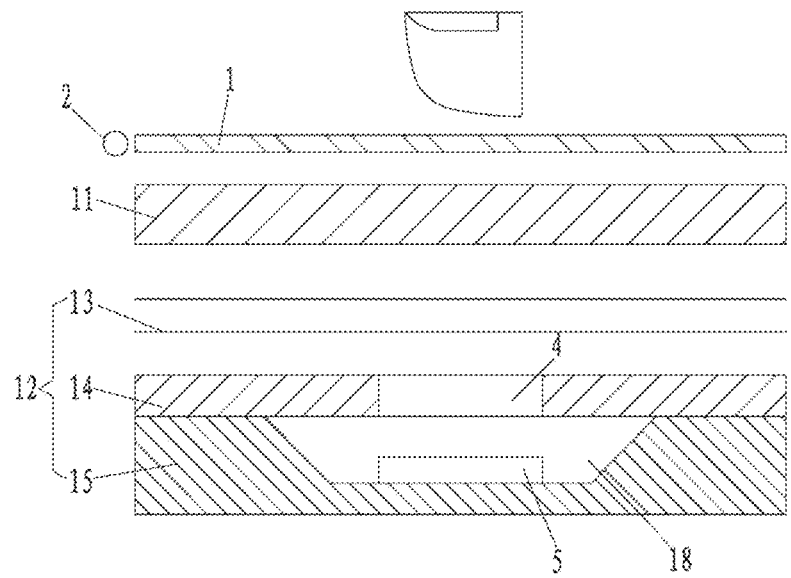
FIG. 12 is a schematic diagram of a liquid crystal terminal device according to a third embodiment of the present disclosure.

FIG. 12 shows a schematic diagram of a liquid crystal terminal device according to a third embodiment of the present disclosure, of which the is mostly the same as that in the embodiment shown in FIG. 10. The difference is that an image sensor 5 is disposed within a concave portion 18 on an upper surface of the back plate 15; the reflective sheet 14 is taken as a pinhole imaging plate; at least one imaging pinhole 4 is disposed on the reflective sheet 14 at a position corresponding to the image sensor 5; the imaging pinhole 4 is disposed to be spaced apart from the image sensor 5; and a light transmitting window is disposed on the optical film 13 at a position corresponding to the imaging pinhole 4.

In acquiring a fingerprint or palmprint, the LCD panel 11 is in a transparent state in response to a control signal.

At least part of light from the light source 2 enters and propagates inside the light guide plate 1 through TIR.

An image of a finger on an upper surface of the light guide plate 1 is acquired by the image sensor 5 of the image scanner through the imaging pinhole 4, the light transmitting window on the optical film 13, the LCD panel 11 and the light guide plate 1.

Figure 13:
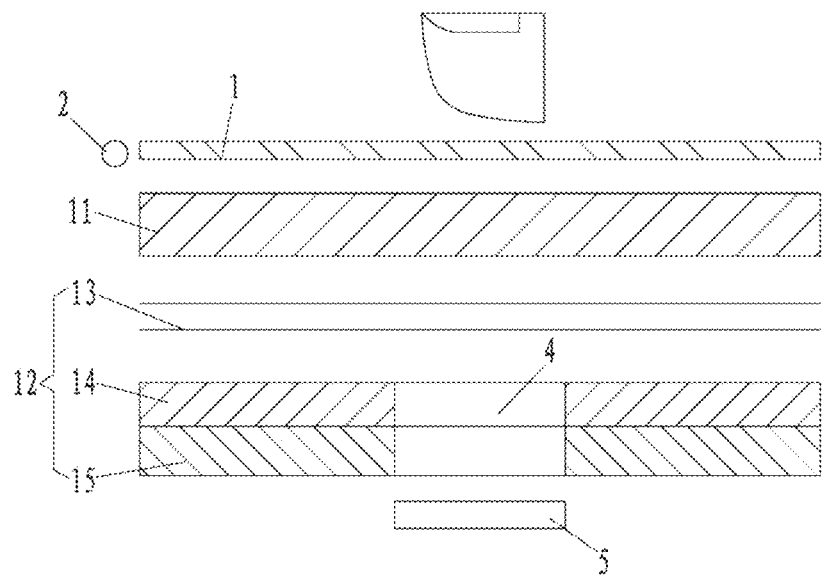
FIG. 13 is a schematic diagram of a liquid crystal terminal device according to a fourth embodiment of the present disclosure.

FIG. 13 shows a schematic diagram of a LCD terminal device according to a fourth embodiment of the present disclosure, of which the structure is mostly the same as that in the embodiment shown in FIG. 11. The difference is that an image sensor 5 is disposed at a position corresponding to the LCD panel 11 at a side (that is, the lower surface) of the back plate 15; the reflective sheet 14 and the back plate 15 as a whole is taken as a pinhole imaging plate; an imaging pinhole 4 is disposed on the pinhole imaging plate at a position corresponding to the image sensor 5; and the imaging pinhole 4 is disposed to be spaced apart from the image sensor 5. In a case that the LCD panel 11 is in a transparent state, at least part of light emitted by the light source 2 enters and propagates inside the light guide plate 1 through TIR. An image of a finger on an upper surface of the light guide plate 1 is acquired by using the image sensor 5 of the image scanner through the imaging pinhole 4, the light transmitting window on the optical film 13, the LCD panel 11 and the light guide plate 1.

Figure 14:
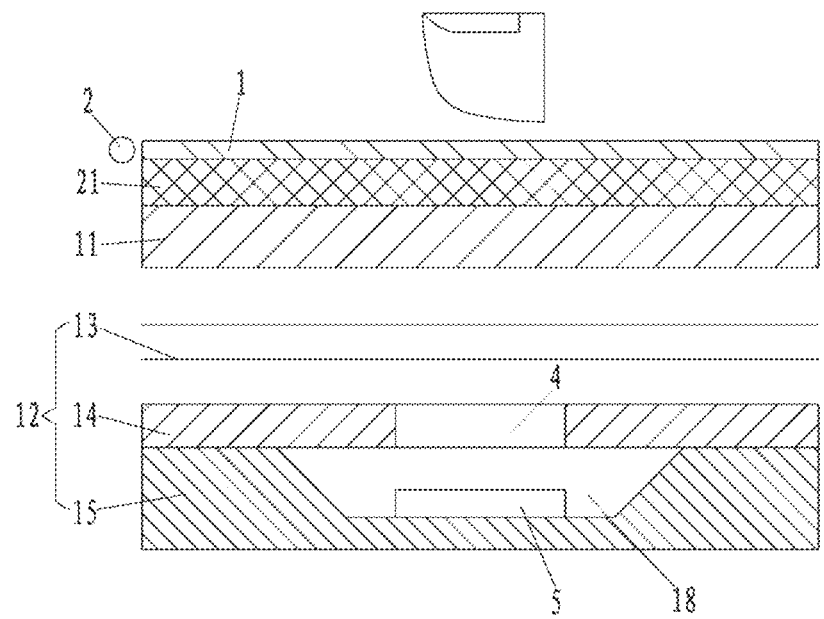
FIG. 14 is a schematic diagram of a liquid crystal terminal device according to a fifth embodiment of the present disclosure.

FIG. 14 shows a schematic diagram of a LCD terminal device according to a fifth embodiment of the present disclosure, of which the structure is mostly the same as that in the embodiment shown in FIG. 12. The difference is that the LCD screen further includes a touch screen 21 located between the LCD panel 11 and the light guide plate 1.

Figure 15:
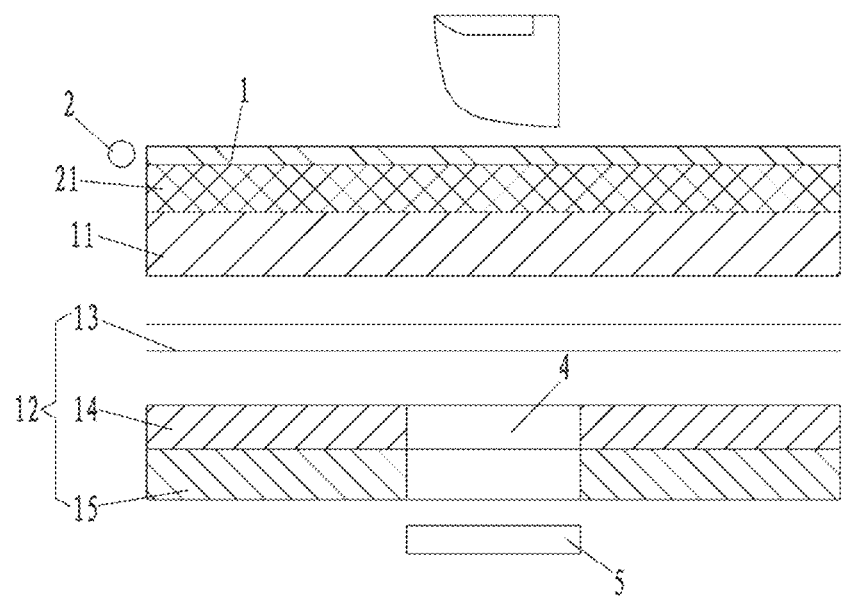
FIG. 15 is a schematic diagram of a liquid crystal terminal device according to a sixth embodiment of the present disclosure.

FIG. 15 shows a schematic diagram of a LCD terminal device according to a sixth embodiment of the present disclosure, of which the structure is mostly the same as that in the embodiment shown in FIG. 13. The difference is that the LCD screen further includes a touch screen 21 located between the LCD panel 11 and the light guide plate 1.

In the embodiments of the liquid crystal terminal device shown in FIG. 12 to FIG. 15 described above, an aperture of the imaging pinhole 4 is in a range from 0.001 mm to 1 mm. For the best imaging effects, shorter imaging distance, processing and other considerations, the aperture of the imaging pinhole 4 may be chosen within the range from 0.01 mm to 0.1 mm, but preferably 0.05 mm. The thickness of the pinhole imaging plate 3 is in a range from 0.005 mm to 5 mm, and preferably, in the range from 0.001 mm to 5 mm, and the thickness of the light guide plate 1 is in a range from 0.1 mm to 5 mm. An optical filter may be disposed between the imaging pinhole 4 and the image sensor 5 to control the uniformity of the light. A correction lens may be disposed on either side or both sides of the imaging pinhole 4 to adjust the light, to obtain a clear image even if the imaging pinhole 4 has a large aperture.

Figure 16:
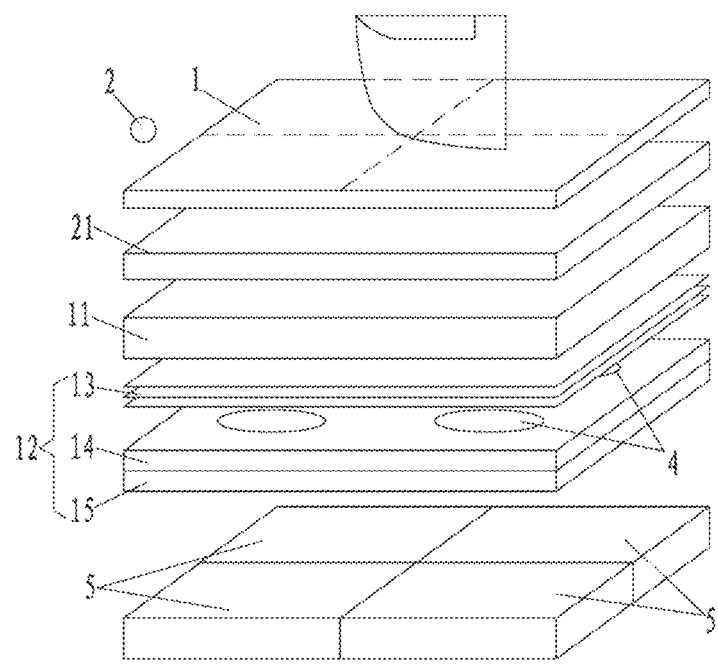
FIG. 16 is a schematic diagram of a liquid crystal terminal device according to a seventh embodiment of the present disclosure.

FIG. 16 is a schematic diagram of a LCD terminal device according to a seventh embodiment of the present disclosure, of which the structure is mostly the same as that in the embodiment shown in FIG. 15. The difference is that the reflective sheet 14 and the back plate 15 as a whole is taken as a pinhole imaging plate, and multiple imaging pinholes 4 are disposed on the pinhole imaging plate. In this embodiment, the number of the imaging pinholes 4 is set to be four, the number of the image sensors 5 is set to be four, and each of the image sensors 5 corresponds to one of the imaging pinholes 4.

An image acquisition method for the LCD terminal device includes the following steps.

Figure 17:
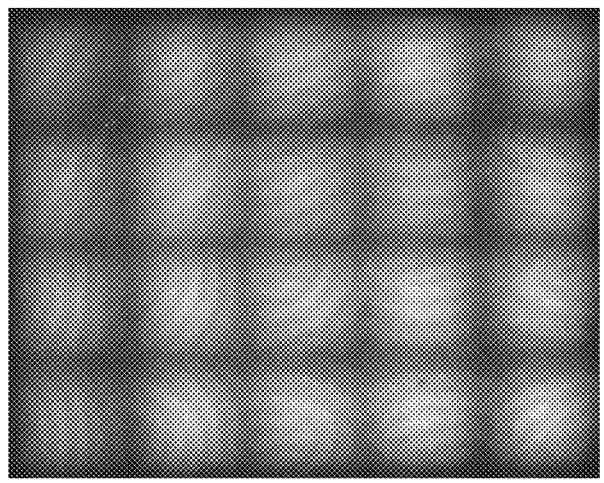
FIG. 17 is a schematic diagram of multiple pinhole images collected by the liquid crystal terminal device shown in FIG. 16.
Figure 18:
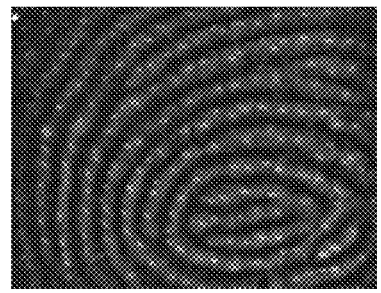
FIG. 18 is a complete fingerprint image stitched from the pinhole images shown in FIG. 17.

The LCD panel 11 is put into a transparent state in response to a control signal;

At least part of light emitted by the light source 2 at the left side of the light guide plate 1 enters and propagates inside the light guide plate 1 through TIR;

Multiple scanning regions corresponding to multiple imaging pinholes are established for the objects above of the light guide plate 1, wherein adjacent scanning regions are overlapping with each other, where the number of the scanning regions in this embodiment is four;

Images of partial fingerprints in the respective scanning regions are acquired one by one by controlling the four image sensors 5 to work one after the other, through the corresponding imaging pinhole 4, the light transmitting window on the optical film 13, the LCD panel 11, the touch screen 21 and the light guide plate 1. For example, reference may be made to FIG. 17, in which 20 partial fingerprint images are shown; and The images of partial fingerprints in the respective imaging regions are stitched together to obtain a complete fingerprint image. Specifically, overlapping regions in four images of partial fingerprints acquired are cut, and then the four images partial fingerprints are stitched together to obtain a complete fingerprint image. For example, the 20 partial fingerprint images in FIG. 17 are stitched together to the complete fingerprint image in FIG. 18.

The control signal described above may be a control signal obtained by the touch screen 21, a control signal obtained by touching a key, a control signal obtained in response to a remote signal, or the similar.

In the embodiments described above of the LCD terminal device, a fingerprint is the scanned object, but generally the object may be any other planar or three-dimensional object.

Figure 19:
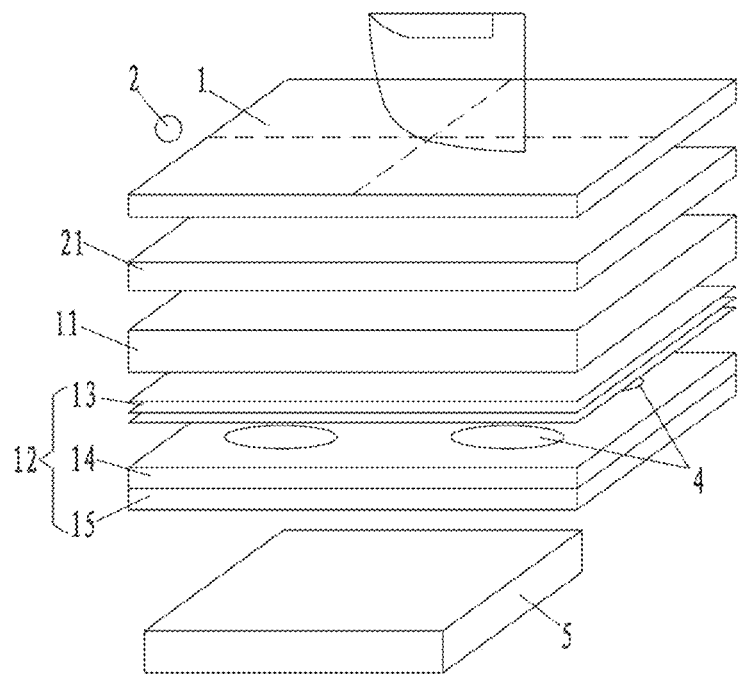
FIG. 19 is a schematic diagram of a liquid crystal terminal device according to an eighth embodiment of the present disclosure.

FIG. 19 shows a schematic diagram of a LCD terminal device according to an eighth embodiment of the present disclosure, of which the structure is mostly the same as that in the embodiment shown in FIG. 16. The difference is that the number of the image sensors 5 is one.

An image acquisition method for the LCD terminal device includes the following steps.

The LCD panel 11 is put into a transparent state in response to a control signal.

At least part of light emitted by the light source 2 enters and propagates inside the light guide plate 1 through TIR.

Multiple scanning regions corresponding to multiple imaging pinholes are established for the object above of the light guide plate 1, wherein adjacent scanning regions are overlapping with each other, where the number of the scanning regions in this embodiment is four.

The LCD panel 11 is divided into four regions, corresponding to the four scanning regions, respectively. In response to a control signal, the respective LCD regions are put into a transparent state one by one by controlling the four respective LCD regions to work, for example, one after the other, such that the image sensors 5 can acquire the partial fingerprint images in the corresponding scanning region through the imaging pinhole 4 and the corresponding liquid crystal region. Thus, partial fingerprint images in the liquid crystal regions can be acquired in turn. Here, partial fingerprint images in the respective imaging regions are not overlapped with each other.

The images of partial fingerprints in the respective imaging regions are stitched together to obtain a complete fingerprint image.

Figure 20:
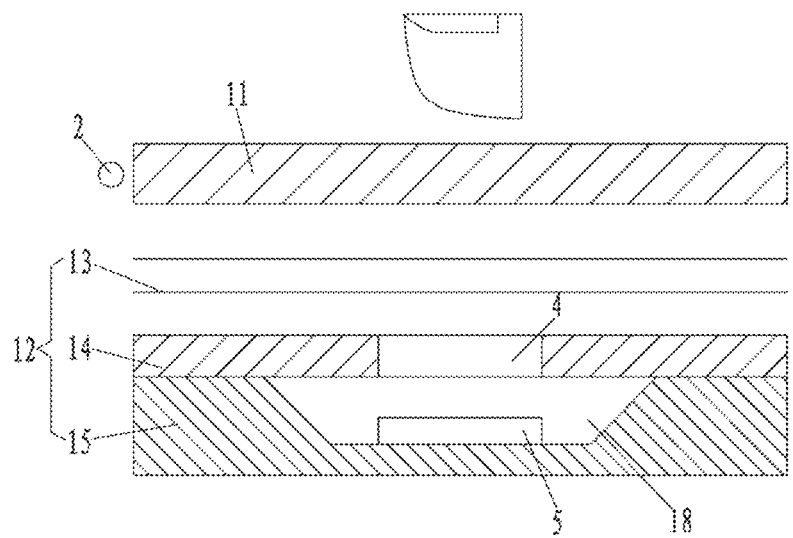
FIG. 20 is a schematic diagram of a liquid crystal terminal device according to a ninth embodiment of the present disclosure.

FIG. 20 shows a schematic diagram of a liquid crystal terminal device according to a ninth embodiment of the present disclosure, of which the structure is mostly the same as that in the embodiment shown in FIG. 12. The difference is, that in this embodiment, the LCD panel 11 is used as the light guide plate, and a light source 2 is disposed at the left side of the LCD panel 11.

In use, the LCD panel 11 is put into the light-transmitting state while the light source 2 is tuned on, so that at least part of light emitted from the light source 2 enters and propagates inside the LCD panel 11 through TIR. An image of an object on or above the LCD panel 11 is acquired by using the image sensor 5 located between a reflective sheet 14 and a back plate 15 through an imaging pinhole 4 on a reflective sheet 14, a light transmitting window on a optical film 13 and the LCD panel 11. In this embodiment, the object is a fingerprint, and may also be a palmprint or a human face.

Figure 21:
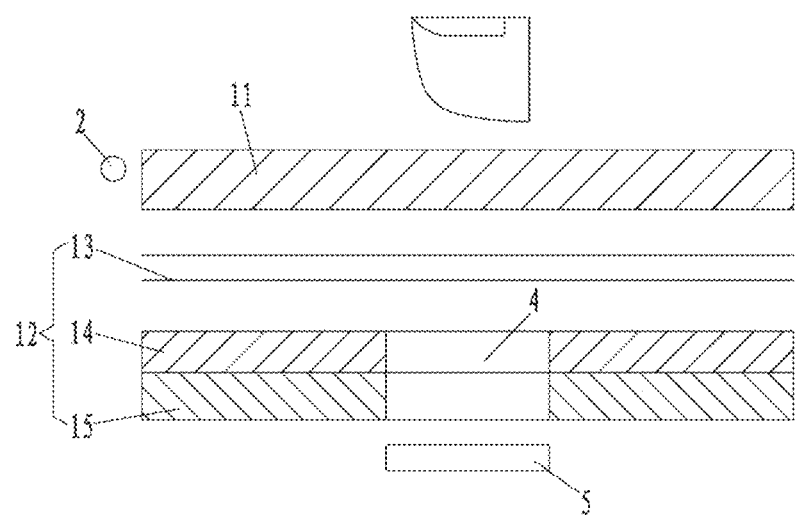
FIG. 21 is a schematic diagram of a liquid crystal terminal device according to a tenth embodiment of the present disclosure.

FIG. 21 shows a schematic diagram of a LCD terminal device according to a tenth embodiment of the present disclosure, of which the structure is mostly the same as that in the embodiment shown in FIG. 13. The difference is that, in this embodiment, the LCD panel 11 is used as the light guide plate, and a light source 2 is disposed at the left side of the LCD panel 11.

In use, the LCD panel 11 is put into the transparent state while the light source 2 is turned on, so that at least part of light emitted from the light source 2 enters and propagates inside the LCD panel 11 through TIR. An image of an object (fingerprint or palmprint) on or above the LCD panel 11 is acquired by using a image sensor 5 located below a back plate 15 through a reflective sheet 14, an imaging pinhole 4 on a back plate 15, a light transmitting window on a optical film 13 and the LCD panel 11.

In the above-described embodiments as shown in FIG. 12 to FIG. 21, a distance from a surface of the light guide plate away from the pinhole imaging plate to the center plane of the imaging pinhole is object distance $h_{object}$, and the object distance $h_{object}$ satisfies the formula of $$h_{object} \geq \frac{\sqrt{2}\,r}{2tg(\alpha/2)},$$

where r represents a distance between the centers of two adjacent imaging pinholes, and α represents the angular field of view of the imaging pinhole. Furthermore, the distance r between the centers of two adjacent imaging pinholes satisfies the formula of $r \geq 2 \cdot h_{image} tg(\alpha/2)$, wherein $h_{image}$ represents an image distance, which is a distance from the image sensor to the center plane of the imaging pinhole, and α represents the angular field of view of the imaging pinhole.

The above embodiments are only the preferred embodiments of the present disclosure and are not intended to define the scope of protection of the present disclosure. Any variations or substitutions which can be readily envisaged by those skilled in the art without departing from the spirit of the invention shall fall into the scope of the invention. Therefore, the protection scope of the invention should be defined according to the appended claims.

What is claimed is:

1. An image acquisition apparatus, comprising:
   a light guide plate;
   a light source for emitting light into the light guide plate, wherein the light source is disposed at one side of the light guide plate;
   a pinhole imaging plate disposed to be spaced apart from the light guide plate, wherein the pinhole imaging plate has at least one imaging pinhole; and
   an image sensor for acquiring an image of an object above the light guide plate, wherein the image sensor is disposed to be spaced apart from the pinhole imaging plate;
   wherein, vertical distance from a surface of the light guide plate away from the pinhole imaging plate to a center plane of the pinhole imaging plate is defined as object distance $h_{object}$ and the object distance $h_{object}$ satisfies a formula of $$h_{object} \geq \frac{\sqrt{2}\,r}{2tg(\alpha/2)},$$

wherein r represents distance between centers of two adjacent imaging pinholes, and α represents angular field of view of the imaging pinhole, wherein the image acquisition apparatus is configured for:
making at least part of light emitted by the light source enter and propagate inside the light guide plate through total internal reflection;
establishing multiple scanning regions corresponding to multiple imaging pinholes for the object above the light guide plate, wherein adjacent scanning regions are overlapping with each other;
capturing multiple imaging regions corresponding to multiple imaging pinholes by the image sensor as partial images of the object above the light guide plate being scanned in corresponding scanning regions, wherein the partial images do not overlap with each other; and
stitching together the partial images in each of the imaging regions to obtain a complete image of the object being scanned.

2. The image acquisition apparatus according to claim 1, wherein, distance r between centers of two adjacent imaging pinholes satisfies a formula of $r \geq 2 \cdot h_{image} tg(\alpha/2)$, wherein $h_{image}$ represents image distance, which is vertical distance from the image sensor to a center plane of the pinhole imaging plate, and α represents angular field of view of the imaging pinhole.

3. A terminal device, comprising the image acquisition apparatus according to claim 1.

4. A terminal device, comprising the image acquisition apparatus according to claim 2.

5. An image acquisition method for an image acquisition apparatus, the method comprising:
making at least part of light emitted by a light source enter and propagate inside a light guide plate through total internal reflection;
establishing multiple scanning regions corresponding to multiple imaging pinholes for the object above the light guide plate, wherein adjacent scanning regions are overlapping with each other;
capturing multiple imaging regions corresponding to multiple imaging pinholes by the image sensor as partial images of the object above the light guide plate being scanned in corresponding scanning regions, wherein the partial images do not overlap with each other; and
stitching together the partial images in each of the imaging regions to obtain a complete image of the object being scanned,
wherein the image acquisition apparatus comprises:
the light guide plate;
the light source for emitting light into the light guide plate, wherein the light source is disposed at one side of the light guide plate;
a pinhole imaging plate disposed to be spaced apart from the light guide plate, wherein the pinhole imaging plate has at least one imaging pinhole; and
an image sensor for acquiring an image of an object above the light guide plate, wherein the image sensor is disposed to be spaced apart from the pinhole imaging plate;
wherein, vertical distance from a surface of the light guide plate away from the pinhole imaging plate to a center plane of the pinhole imaging plate is defined as object distance $h_{object}$, and the object distance $h_{object}$ satisfies a formula of $$h_{object} \geq \frac{\sqrt{2}\,r}{2tg(\alpha/2)},$$

wherein r represents distance between centers of two adjacent imaging pinholes, and $\alpha$ represents angular field of view of the imaging pinhole, and distance r between centers of two adjacent imaging pinholes satisfies a formula of $r \geq 2 \cdot h_{image} tg(\alpha/2)$, wherein $h_{image}$ represents image distance, which is vertical distance from the image sensor to a center plane of the pinhole imaging plate, and $\alpha$ represents angular field of view of the imaging pinhole.

* * * * *

UNITED STATES PATENT AND TRADEMARK OFFICE
CERTIFICATE OF CORRECTION

PATENT NO. : 10,083,335 B2
APPLICATION NO. : 15/320243
DATED : September 25, 2018
INVENTOR(S) : Mingfang Zhang Page 1 of 1

It is certified that error appears in the above-identified patent and that said Letters Patent is hereby corrected as shown below:

Please amend the word "tuned" to -- "turned" -- (Column 16, Line 55).

Signed and Sealed this
Twenty-seventh Day of November, 2018

Andrei Iancu
*Director of the United States Patent and Trademark Office*